(12) United States Patent
Ross, Jr. et al.

(10) Patent No.: US 8,785,650 B2
(45) Date of Patent: Jul. 22, 2014

(54) METHODS FOR PREPARING 3-SUBSTITUTED-6-TRIFLUOROMETHYL PYRIDINES AND METHODS FOR USING 6-TRICHLOROMETHYL HALOGENATED PYRIDINES

(71) Applicant: Dow AgroSciences LLC, Indianapolis, IN (US)

(72) Inventors: Ronald Ross, Jr., Zionsville, IN (US); James M. Renga, Indianapolis, IN (US); Douglas Bland, Mason, OH (US); Gary Roth, Midland, MI (US); Alexander P. Fung, Martinez, CA (US); Clark S. Davis, Freeland, MI (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/839,373

(22) Filed: Mar. 15, 2013

(65) Prior Publication Data

US 2013/0261310 A1  Oct. 3, 2013

Related U.S. Application Data

(60) Provisional application No. 61/618,370, filed on Mar. 30, 2012.

(51) Int. Cl.
*C07D 211/72* (2006.01)
(52) U.S. Cl.
USPC .......................................................... 546/345

(58) Field of Classification Search
None
See application file for complete search history.

(56) References Cited

U.S. PATENT DOCUMENTS

| 4,480,102 A | 10/1984 | Werner et al. |
| 4,590,279 A | 5/1986 | Fung et al. |
| 6,548,511 B1 | 4/2003 | Hirai et al. |

FOREIGN PATENT DOCUMENTS

| WO | 2007095229 A2 | 8/2007 |
| WO | WO 2007095229 A2 * | 8/2007 |

OTHER PUBLICATIONS

CASREACT Accession No. 148 7887 (2009).*
International Search Report and Written Opinion for International Application No. PCT/US2013/032270, mailed Jul. 25, 2013.

* cited by examiner

*Primary Examiner* — Heidi Reese
(74) *Attorney, Agent, or Firm* — Carl D. Corvin; TraskBritt P.C.

(57) ABSTRACT

3-substituted-6-trifluoromethyl pyridines are useful synthetic intermediates in the preparation of the N-substituted (6-haloalkylpyridin-3-yl)alkyl sulfoximines, which are useful in forming potent insecticides. Methods of forming such 3-substituted-6-trifluoromethyl pyridines are disclosed. Also disclosed are methods of using 6-trichloromethyl halogenated pyridines to form 3-substituted-6-trifluoromethyl pyridines are disclosed.

23 Claims, No Drawings

METHODS FOR PREPARING 3-SUBSTITUTED-6-TRIFLUOROMETHYL PYRIDINES AND METHODS FOR USING 6-TRICHLOROMETHYL HALOGENATED PYRIDINES

CROSS-REFERENCE TO RELATED APPLICATION

This application claims the benefit of U.S. Provisional Patent Application Ser. No. 61/618,370, filed Mar. 30, 2012, the disclosure of which is hereby incorporated herein in its entirety by this reference.

TECHNICAL FIELD

Embodiments of the present disclosure relate to methods of forming 3-substituted-6-trifluoromethyl pyridines and to methods of using 6-trichloromethyl halogenated pyridines to form 3-substituted-6-trifluoromethyl pyridines.

BACKGROUND

N-substituted (6-haloalkylpyridin-3-yl)alkyl sulfoximines are useful in controlling insects and certain other invertebrates, particularly aphids and other sucking insects, as described in International Application Publication No. WO 2007/095229, published Aug. 23, 2007. 3-Substituted-6-trifluoromethyl pyridines are useful synthetic intermediates in the preparation of the N-substituted (6-haloalkylpyridin-3-yl)alkyl sulfoximines.

BRIEF SUMMARY

An embodiment of the present disclosure includes a method of forming a compound of Formula I, i.e., a 3-substituted-6-trifluoromethyl pyridine:

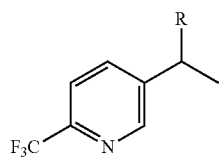

I wherein R represents hydrogen, an alkyl group, or an aryl group;
from compounds of Formula II, i.e., a 2,3-dihalo-(4-halo)-6-trichloromethyl pyridine:

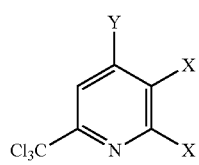

II wherein
  X represents a halogen; and
  Y represents hydrogen or a halogen.

In particular embodiments, compounds of Formula I independently include those in which R represents hydrogen, such that the compound of Formula I is a 3-ethyl-6-trifluoromethyl pyridine.

In other particular embodiments, compounds of Formula II independently include those in which X represents chlorine and Y represents hydrogen, such that the compound of Formula II is a 2,3-dichloro-6-trichloromethyl pyridine.

The present disclosure includes a method of forming a compound of Formula I from a compound of Formula II by fluorinating the compound of Formula II to form a compound of Formula III, i.e., a 2,3-dihalo-(4-halo)-6-trifluoromethyl pyridine:

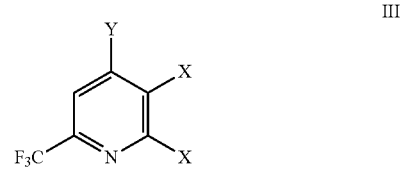

III according to Scheme 1, as follows:

Scheme 1

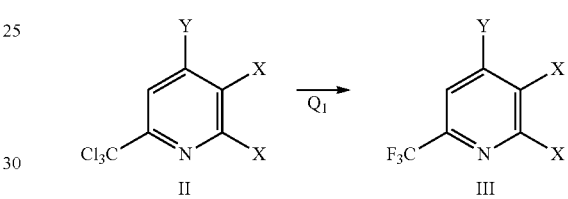

wherein
$Q_1$ represents a fluorinating agent, e.g., antimony pentafluoride or hydrogen fluoride.

In a particular embodiment, compounds of Formula III independently include those in which X represents chlorine and Y represents hydrogen, such that the compound of Formula III is a 2,3-dichloro-6-trifluoromethyl pyridine.

Another particular embodiment of the present disclosure includes a method of using antimony pentafluoride to fluorinate a 2,3-dihalo-(4-halo)-6-trichloromethyl pyridine to form a 2,3-dihalo-(4-halo)-6-trifluoromethyl pyridine, e.g., reacting a 2,3-dichloro-6-trichloromethyl pyridine with antimony pentafluoride to form a 2,3-dichloro-6-trifluoromethyl pyridine.

Still another particular embodiment of the present disclosure includes a method of using hydrogen fluoride to fluorinate a 2,3-dihalo-(4-halo)-6-trichloromethyl pyridine to form a 2,3-dihalo-(4-halo)-6-trifluoromethyl pyridine, e.g., reacting a 2,3-dichloro-6-trichloromethyl pyridine with hydrogen fluoride to form a 2,3-dichloro-6-trifluoromethyl pyridine.

The method of forming a 3-substituted-6-trifluoromethyl pyridine may further include reducing the compound of Formula III to form a compound of Formula IV, i.e., a 3-halo-6-trifluoromethyl pyridine:

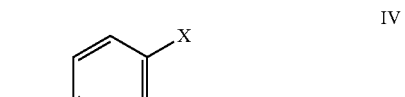

IV according to Scheme 2, as follows:

Scheme 2

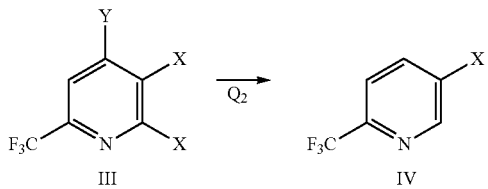

wherein

Q₂ represents a reducing agent. The reducing agent may include, but is not limited to, hydrazine (also referred to in the art as diazane) and sodium hypochlorite (commonly known as and referred to herein as "bleach") or may include copper and propionic acid.

In a particular embodiment, compounds of Formula IV independently include those in which X represents chlorine, such that the compound of Formula IV is a 3-chloro-6-trifluoromethyl pyridine.

Another particular embodiment of the present disclosure includes a method of treating a 2,3-dihalo-(4-halo)-6-trifluoromethyl pyridine with hydrazine and bleach to form a 3-halo-6-trifluoromethyl pyridine (e.g., reacting a 2,3-dichloro-6-trifluoromethyl pyridine with hydrazine and bleach to form a 3-chloro-6-trifluoromethyl pyridine).

Still another particular embodiment of the present disclosure includes a method of treating a 2,3-dihalo-(4-halo)-6-trifluoromethyl pyridine with copper and propionic acid to form a 3-halo-6-trifluoromethyl pyridine (e.g., reacting a 2,3-dichloro-6-trifluoromethyl pyridine with copper and propionic acid to form a 3-chloro-6-trifluoromethyl pyridine).

The method may further include a Grignard reaction of the compound of Formula IV to form the compound of Formula I according to Scheme 3, as follows:

Scheme 3

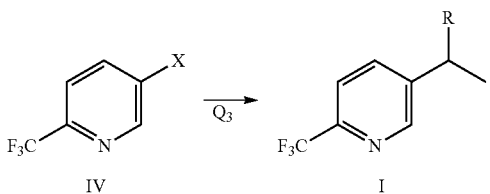

wherein

Q₃ represents a Grignard reagent in the presence of a metal-based (e.g., nickel-based or iron-based) catalyst.

A particular embodiment of the present disclosure includes a method of reacting a 3-halo-6-trifluoromethyl pyridine with ethyl magnesium bromide in the presence of a nickel- or iron-based catalyst to form a 3-substituted-6-trifluoromethyl pyridine (e.g., reacting a 3-chloro-6-trifluoromethyl pyridine with ethyl magnesium bromide in the presence of a nickel- or iron-based catalyst to form a 3-ethyl-6-trifluoromethyl pyridine).

Accordingly, methods of forming 3-substituted-6-trifluoromethyl pyridines are disclosed. Also disclosed are methods of using 2,3-dihalo-(4-halo)-6-trichloromethyl pyridines to form 3-substituted-6-trifluoromethyl pyridines.

DETAILED DESCRIPTION

As used herein, the term "alkyl" refers to an acyclic, saturated, branched or unbranched substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

As used herein, the term "aryl" refers to a cyclic, aromatic substituent consisting of hydrogen and carbon.

As used herein, the term "halo" refers to fluoro, chloro, bromo, and iodo.

As used herein, the term "halogen" refers to fluorine, chlorine, bromine, and iodine.

As used herein, the term Grignard reagent refers to an organomagnesium halide.

Compounds of Formula I, as follows, are useful intermediates in forming compounds used in preparing agricultural chemicals, such as insecticides:

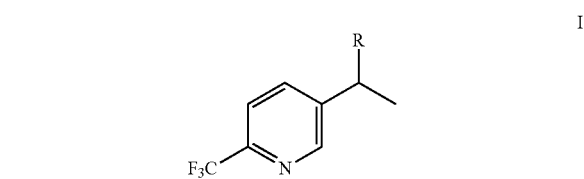

Wherein R represents hydrogen, an alkyl group, or an aryl group.

Such 3-substituted-6-trifluoromethyl pyridines include a pyridine ring having a trifluoromethyl group at the 6 position and a hydrocarbon substituent (substitute group) at the 3 position. In particular embodiments, an ethyl group may be at the 3 position, such that the compound may be a 3-ethyl-6-trifluoromethyl pyridine.

Compounds of Formula I may be formed using compounds of Formula II, as follows:

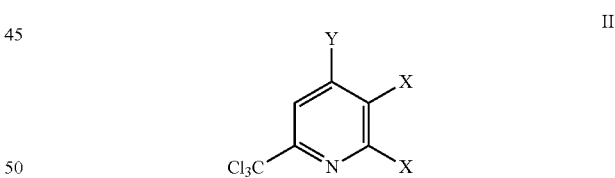

wherein

X represents a halogen; and

Y represents hydrogen or a halogen.

Such 2,3-dihalo-(4-halo)-6-trichloromethyl pyridine include a pyridine ring having a trichloromethyl group at the 6 position, hydrogen or a halogen at the 4 position, and a halogen at each of the 2 and 3 positions. In particular embodiments, hydrogen may be at the 4 position and chlorine may be at each of the 2 and 3 positions, such that the compound may be a 2,3-dichloro-6-trichloromethyl pyridine.

Forming a compound of Formula I from a compound of Formula II may include using the compound of Formula II to form a compound of Formula III, wherein a compound of Formula III is as follows:

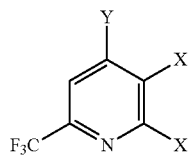

III

Using a compound of Formula II to form a compound of Formula III may be in accordance with Scheme 1, as follows:

Scheme 1

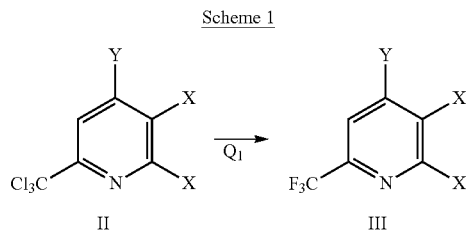

wherein $Q_1$ represents a fluorinating agent (e.g., antimony pentafluoride or hydrogen fluoride).

As shown in Scheme 1, a compound of Formula III (i.e., a 2,3-dihalo-(4-halo)-6-trifluoromethyl pyridine), can be prepared by fluorinating a compound of Formula II, i.e., a 2,3-dihalo-(4-halo)-6-trichloromethyl pyridine. The method of Scheme 1 includes reacting a compound of Formula II with a fluorinating agent, such as antimony pentafluoride or hydrogen fluoride, to form a compound of Formula III.

The method of Scheme 1 includes reacting the trichloromethyl group at the 6 position of the pyridine ring of the compound of Formula II with the fluorinating agent to form a trifluoromethyl group at the 6 position of the pyridine ring. Thus, the compound of Formula III may be the trifluoromethyl derivative of the trichloromethyl compound of Formula II.

The method of Scheme 1 may further include introducing the fluorinated agent in the presence of a catalyst, such as iron (III) chloride.

In a particular embodiment, X represents chlorine, Y represents hydrogen, and $Q_1$ represents hydrogen fluoride. The method of this embodiment of Scheme 1 is illustrated in Example 1.

In another particular embodiment, X represents chlorine, Y represents hydrogen, and $Q_1$ represents antimony pentafluoride. The method of this embodiment of Scheme 1 is illustrated in Example 2.

Forming a compound of Formula I from a compound of Formula II may further include using a compound of Formula III to form a compound of Formula IV, wherein a compound of Formula IV is as follows:

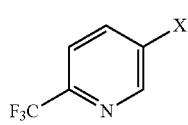

IV

Using a compound of Formula III to form a compound of Formula IV may be in accordance with Scheme 2, as follows:

Scheme 2

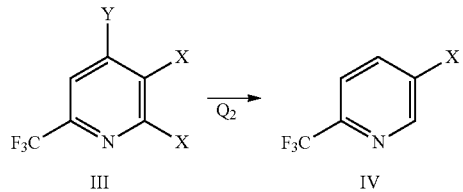

wherein $Q_2$ represents a reducing agent. For example, the reducing agent may include hydrazine (also referred to in the art as diazane) and bleach or may include represents copper and propionic acid. In embodiments utilizing copper and propionic acid, copper powder in propionic acid may be used. In some such embodiments, two equivalents of copper powder in heated propionic acid may be used.

As shown in Scheme 2, a compound of Formula IV (i.e., a 3-halo-6-trifluoromethyl pyridine), can be prepared by reducing a compound of Formula III (i.e., a 2,3-dihalo-(4-halo)-6-trifluoromethyl pyridine). The method of Scheme 2 includes reacting a compound of Formula III with either hydrazine and bleach, or with copper and propionic acid to form a compound of Formula IV.

The method of Scheme 2 includes reducing the compound of Formula III to remove halogens at the 2 position and, if present in the compound of Formula III, at the 4 position to form the compound of Formula IV, which does not include a halogen at the 2 or the 4 position, but includes a halogen at the 3 position of the pyridine ring. Thus, the method of Scheme 2 is a mono-dehalogenation and cross-coupling process.

In a particular embodiment, X represents chlorine, Y represents hydrogen, and $Q_2$ represents hydrazine and bleach. The method of this embodiment of Scheme 2 is illustrated in Example 3.

In another particular embodiment, X represents chlorine, Y represents hydrogen, and $Q_2$ represents copper and propionic acid. The method of this embodiment of Scheme 2 is illustrated in Example 4.

Accordingly, the method of Scheme 2 provides a method of using a compound of Formula III to form a compound of Formula IV. Also, the combined methods of Schemes 1 and 2 provide a method of using a compound of Formula II to form a compound of Formula IV. Formed compounds may or may not be isolated between combined schemes.

Forming a compound of Formula I from a compound of Formula II may further include using a compound of Formula IV to form a compound of Formula I in accordance with Scheme 3, as follows:

Scheme 3

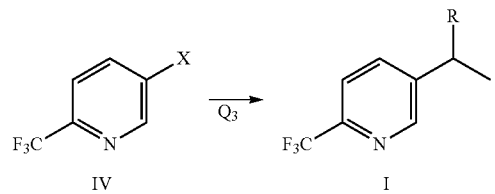

wherein $Q_3$ represents a Grignard reagent in the presence of a metal-based (e.g., a nickel-based or an iron-based) catalyst.

As shown in Scheme 3, a compound of Formula I (i.e., a 3-substituted-6-trifluoromethyl pyridine), can be prepared by subjecting a compound of Formula IV (i.e., a 3-halo-6-trifluoromethyl pyridine), to a Grignard reaction. The method of Scheme 3 includes reacting a compound of Formula IV with a Grignard reagent in the presence of a metal-based catalyst to form a compound of Formula I.

The method of Scheme 3 includes contacting the halogen at the 3 position of the pyridine ring of the compound of Formula IV with the Grignard reagent to substitute the halogen for a hydrocarbon substituent at the 3 position of the pyridine ring.

The Grignard reagent of Scheme 3 may be an alkyl or aryl magnesium bromide, e.g., an ethyl magnesium bromide. The metal-based catalyst may be, for example and without limitation, Bis-triphenylphosphine nickel (II) dichloride, iron (III) acetylacetonate, iron (III) phthalocyanine, or iron (III) chloride.

In a particular embodiment, X represents chlorine, R represents hydrogen, and $Q_3$ represents ethyl magnesium bromide in the presence of a nickel-based catalyst. The method of this embodiment of Scheme 3 is illustrated in Example 6.

In another particular embodiment, X represents chlorine, R represents hydrogen, and $Q_3$ represents ethyl magnesium bromide in the presence of an iron-based catalyst. The method of this embodiment of Scheme 3 is illustrated in each of Examples 5 and 7 through 9.

Accordingly, the method of Scheme 3 provides a method of using a compound of Formula IV to form a compound of Formula I. Also, the combined methods of Schemes 2 and 3 provide a method of using a compound of Formula III to form a compound of Formula I. Further, the combined methods of Schemes 1 through 3 provide a method of using a compound of Formula II to form a compound of Formula I. Formed compounds may or may not be isolated between combined schemes.

Scheme 4

A particular embodiment of the present disclosure includes a method of forming the compound of Formula I from a compound of Formula III. The method includes a Grignard reaction of the compound of Formula III to form the compound of Formula V. The method further includes reducing the compound of Formula V to form a compound of Formula I, as follows:

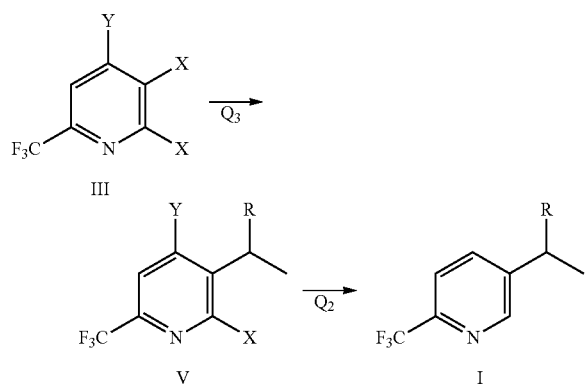

wherein
X represents a halogen;
Y represents hydrogen or a halogen;

R represents hydrogen, an alkyl group, or an aryl group;
$Q_3$ represents a Grignard reagent in the presence of a metal-based (e.g., nickel-based or iron-based) catalyst; and
$Q_2$ represents a reducing agent. The reducing agent may include, but is not limited to, hydrazine (also referred to in the art as diazane) and sodium hypochlorite (commonly known as and referred to herein as "bleach") or may include copper and propionic acid.

As shown in Scheme 4, a compound of Formula V can be prepared by subjecting a compound of Formula III to a Grignard reaction. The method of Scheme 4 includes reacting a compound of Formula III with a Grignard reagent in the presence of a metal-based catalyst to form a compound of Formula V.

The method of Scheme 4 includes contacting the halogen at the 3 position of the pyridine ring of the compound of Formula III with the Grignard reagent to substitute the halogen for a hydrocarbon substituent at the 3 position of the pyridine ring.

The Grignard reagent of Scheme 4 may be an alkyl or aryl magnesium bromide, e.g., an ethyl magnesium bromide. The metal-based catalyst may be, for example and without limitation, Bis-triphenylphosphine nickel (II) dichloride, iron (III) acetylacetonate, iron (III) phthalocyanine, or iron (III) chloride.

As further shown in Scheme 4, a compound of Formula I can be prepared by reducing a compound of Formula V. In a particular embodiment, the method of Scheme 4 includes reacting a compound of Formula V with either hydrazine and bleach, or with copper and propionic acid, to form a compound of Formula I.

The method of Scheme 4 includes reducing the compound of Formula V to remove halogens at the 2 position and, if present in the compound of Formula V, at the 4 position to form the compound of Formula I. Thus, the method of Scheme 4 includes a mono-dehalogenation and cross-coupling process.

In a particular embodiment, X represents chlorine, Y represents hydrogen, and $Q_2$ represents hydrazine and bleach. The method of this embodiment of Scheme 2 is illustrated in Example 3.

Accordingly, methods of forming 3-substituted-6-trifluoromethyl pyridines are disclosed. Also disclosed are methods of using 2,3-dihalo-(4-halo)-6-trichloromethyl pyridines to form 3-substituted-6-trifluoromethyl pyridines.

Another particular embodiment of the present disclosure includes a method of treating a 2,3-dihalo-(4-halo)-6-trifluoromethyl pyridine with hydrazine and bleach to form a 3-halo-6-trifluoromethyl pyridine (e.g., reacting a 2,3-dichloro-6-trifluoromethyl pyridine with hydrazine and bleach to form a 3-chloro-6-trifluoromethyl pyridine).

Still another particular embodiment of the present disclosure includes a method of treating a 2,3-dihalo-(4-halo)-6-trifluoromethyl pyridine with copper and propionic acid to form a 3-halo-6-trifluoromethyl pyridine (e.g., reacting a 2,3-dichloro-6-trifluoromethyl pyridine with copper and propionic acid to form a 3-chloro-6-trifluoromethyl pyridine).

It is recognized that some reagents and reaction conditions disclosed herein or in the chemical literature for preparing compounds of Formulas I, III, IV, and V, or derivatives thereof, may not be compatible with certain functionalities present in the intermediates. In these instances, the incorporation of protection/deprotection sequences or functional group interconversions into the synthesis will aid in obtaining the desired products. The use and choice of the protection groups will be apparent to one skilled in chemical synthesis.

One skilled in the art will recognize that, in some cases, after the introduction of a given reagent as disclosed herein or in the chemical literature, it may be necessary to perform additional routine synthetic steps not described in detail to complete the synthesis of the pyridine compounds described above. One skilled in the art will also recognize that it may be necessary to perform a combination of the steps disclosed herein or in the chemical literature in an order other than that implied by the particular sequence presented to prepare the pyridine compounds described above.

Finally, one skilled in the art will also recognize that pyridine compounds described above and the intermediates thereof described herein or in the chemical literature can be subjected to various electrophilic, nucleophilic, radical, organometallic, oxidation, and reduction reactions to add substituents or modify existing substituents.

The compounds of Formula I have been found to be useful intermediates in the formation of insecticides. International Application Publication No. WO 2007/095229, published Aug. 23, 2007, the disclosure of which is herein incorporated by reference, describes the synthesis of N-substituted (6-haloalkylpyridin-3-yl)alkyl sulfoximines from compounds of Formula I. The publication further describes use of such N-substituted (6-haloalkylpyridin-3-yl)alkyl sulfoximines to form useful insecticides. The term insecticide as used herein means an active ingredient that kills, controls, or otherwise adversely modifies insects.

The following examples are presented to illustrate various embodiments of the present disclosure in more detail. These examples are not be construed as being exhaustive or exclusive as to the scope of this invention.

EXAMPLES

Example 1

Preparation of 2,3-dichloro-6-trifluoromethyl pyridine

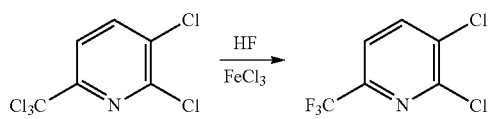

A 480 mL Teflon PFA (perfluoroalkoxy) reaction flask fitted with a PFA reflux condenser, a hydrogen fluoride (HF) bleed tube, and a magnetic stirrer was charged 2,3-dichloro-6-trichloromethyl pyridine (200 g) and iron (III) chloride (8.6 g, 7 mole %). A molar excess of anhydrous hydrogen fluoride (HF) gas was introduced into the reaction mixture at 4 g/hr below the surface of the liquid as the mixture was heated to a temperature of 170° C. and maintained for a period of 34 hours. The progress of the reaction was monitored using gas chromatography (GC). Upon substantial completion of the reaction (94.1% conversion to the trifluoromethyl halogenated pyridine), the reaction mixture was cooled and quenched with ice water (200 g). The organic layer was separated, filtered, and washed with water (2×200 g), neutralized with sodium bicarbonate ($NaHCO_3$), and dried over magnesium sulfate ($MgSO_4$) (127 g). Most of the crude product (123 g) was distilled under reduced pressure (95° C., 300 mmHg) resulting in 2,3-dichloro-6-trifluoromethyl pyridine (95.5%) in addition to 2-fluoro-3-chloro-6-trifluoromethyl pyridine (2.3%) and 2,3-dichloro-6-(chloro-difluoro)methyl pyridine (1.4%). The product was further characterized by spectroscopic methods.

Example 2

Preparation of 2,3-dichloro-6-trifluoromethyl pyridine

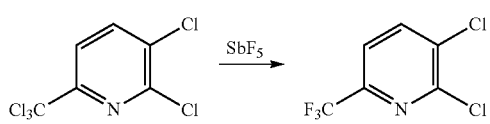

Antimony pentafluoride ($SbF_5$) (96.6 g, 0.446 moles) was charged into a tarred 14/20 addition funnel and weighed inside a glove bag. 2,3-dichloro-trichloromethyl pyridine (168.5 g, 0.635 moles) was charged to a 14/20 three-neck round bottom flask equipped with a nitrogen inlet, a thermometer, and a stirbar. The addition funnel was stoppered and a 10 mL flask was temporarily attached to the bottom before it was removed from the glove bag. The reaction flask was nitrogen purged. The addition funnel was attached to the reaction flask, and the reaction flask was placed in an ambient temperature water bath. Antimony pentafluoride ($SbF_5$) was added at a rate to maintain the temperature between 38° C. and 45° C. until about 57 grams of antimony pentafluoride ($SbF_5$) had been added. At this point, the reaction mass partially solidified, and the temperature rose to 55° C. Analysis of the reaction mass indicated that the reaction was roughly 66% complete. Antimony pentafluoride ($SbF_5$) addition was continued at a rate to control the temperature at approximately 55° C. The mixture was agitated by swirling the flask by hand to slurry the reaction mixture. (Smaller scale experiments had not resulted in solids formation, and mechanical stirring, rather than magnetic stirring, can be performed in this reaction.) Antimony pentafluoride ($SbF_5$) addition was continued until 91 grams (0.420 moles, 0.66 equivalents) had been added. GC analysis did not indicate the presence of the starting material. The mixture was poured into ice water (500 g), and dichloromethane (500 g) was added to dissolve the organics. The solution was filtered to remove antimony salts, and the layers separated. The organic layer was washed with saturated sodium bicarbonate. The aqueous layer was extracted three times with dichloromethane (100 g), and the resulting three dichloromethane layers were combined and washed with saturated sodium bicarbonate. Both of the organic layers were combined, dried over magnesium sulfate, filtered, and concentrated on a rotovap to give 146.3 grams of crude 2,3-dichloro-6-trifluoromethyl pyridine as a liquid that crystallized on standing.

The crude 2,3-dichloro-6-trifluoromethyl pyridine was distilled in an apparatus consisting of a magnetically stirred, 14/20, 250 mL kettle with a 1-piece Vigreaux head with integral condenser, a four fraction distillation receiver, and a heating mantle. Air was used in the condenser to prevent the product freezing in the condenser, but parts of the distillation apparatus were warmed with a heat gun to melt the product as it distilled. The pressure was established at 40 mmHg and maintained throughout the distillation. Four fractions were collected. The first fraction, 4.6 grams, was collected at 94° C. to 95° C. head temperature and consisted of 92 area % 2,3-dichloro-6-trifluoromethyl pyridine with 4% of an unidentified light material. The second fraction, 16.4 grams, was collected at 95° C. head temperature and consisted of 94 area % 2,3-dichloro-6-trifluoromethyl pyridine along with 2.8% of the light compound. The third fraction, 94.5 grams, consisted of 96.4 area % 2,3-dichloro-6-trifluoromethyl pyridine along with 1% light material. The fourth fraction, 6.0 grams, consisted of 93 area % 2,3-dichloro-6-trifluoromethyl pyridine with only heavier components present. The kettle contained 10.7 grams that was 42 area % 2,3-dichloro-6-trifluoromethyl pyridine as determined by GC. The overhead materials crystallized on standing, and the material in the third fraction had a melting point of 39° C. to 41° C. The combined yield for the four overhead fractions (corrected for product GC purity, but not starting material purity) was 85%.

Example 3

Preparation of 3-chloro-6-trifluoromethyl pyridine

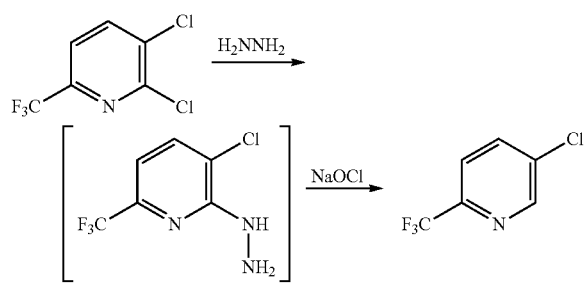

The first and second fractions from the 2,3-dichloro-6-trifluoromethyl pyridine distillation of Example 2 were combined, and the third and fourth fractions of the 2,3-dichloro-6-trifluoromethyl pyridine distillation of Example 2 were combined in this Example to segregate material containing the light impurity.

The first and second fractions of 2,3-dichloro-6-trifluoromethyl pyridine (21.0 g, 0.097 mol) were dissolved in 2-propanol (103 g). Hydrazine hydrate ($H_2NNH_2 \cdot H_2O$) (21.1 g) was added, and the bottle containing the mixture was placed in a water bath (80° C.). A precipitate formed as the solution was warming, which then melted to form a second liquid layer.

The third and fourth fractions of 2,3-dichloro-6-trifluoromethyl pyridine (100.5 g, 0.465 mol) were dissolved in 2-propanol (474 g). Hydrazine hydrate ($H_2NNH_2 \cdot H_2O$) (112.6 g) was added to the bottle, and the mixture was placed in a water bath (80° C.). A precipitate formed as the solution was warming, which then melted to form a second liquid layer.

The reaction mixtures were left in the water bath for 8 hours at 80° C., after which sampling indicated about 6.5% starting material remained. The bath was turned off and left overnight, after which sampling indicated about 2.5% starting material remained. The mixtures were reheated at 80° C. for 3 hours, after which there was less than 0.5% starting material present.

The bottom layers from both the reaction masses were removed by pipette; 7.3 g from the reaction mass from the combination of the first and second fractions and 56.2 g from the reaction mass from the combined third and fourth fractions. Dissolving the bottom layer from the reaction masses in water, extracting with dichloromethane, and stripping the dichloromethane did not result in isolation of any organic material. The second layer was assumed to be hydrazine hydrochloride. The reaction mass resulting from reaction of the first and second fractions was concentrated on a rotovap until almost all of the solvent was removed, then poured into water (150 mL). The solids were isolated and washed twice with water (50 mL), then dried under vacuum to give 19.93 g. The reaction mass resulting from reaction of the third and fourth fractions was concentrated on the rotovap until almost all of the solvent was removed, then poured into water (500 mL). The solids were isolated, washed twice with water (100 mL), and then dried under vacuum to give 93.7 g of a white solid. GC analysis indicated a 98.6 area %. The hydrazine derivative had a melting point of 115° C. to 117° C.

The combined yield for both batches was 98.3%, corrected for starting material GC purity and product GC purity, although the material was not rigorously dried or analyzed for moisture.

19.91 g of 2-hydrazino-3-chloro-6-trifluoromethyl pyridine from the small batch and 30.19 g from the large batch were combined (50.10 g total, 0.237 mol) in a 2 L, three-neck flask with a mechanical stirrer and an addition funnel. Dichloromethane (190 g) and sodium hydroxide (237 g, 1N solution) were added to the flask. Sodium hypochlorite (NaOCl) (354 g, 0.238 mol, 5% solution) was charged to the addition funnel. The sodium hypochlorite solution was added over 1 hour as the solution turned yellow, then orange, and then purple-brown. The conversion was approximately 36% at the end of the sodium hypochlorite addition. The solution was stirred for an additional 6.5 hours, at which point the conversion was about 98%. Agitation was stopped and the solution was left overnight. The next morning, sodium hypochlorite (9 g, 0.006 mol, 5% solution) was added, and the solution was stirred for 1.5 hours, at which point sampling indicated that there was less than 1% starting material. The layers were separated and the aqueous layer was extracted twice with dichloromethane (100 mL). The organic layers were combined, washed with water, dried with magnesium sulfate, filtered, and concentrated on the rotovap to give 46.44 g of crude 3-chloro-6-trifluoromethyl pyridine.

The remaining 2-hydrazino-3-chloro-6-trifluoromethyl pyridine (63.36 g, 0.299 mol) was dissolved in dichloromethane (600 g) and charged to a 2 L, three-neck flask with a mechanical stirrer. Sodium hydroxide (300 g, 1N solution) was added, and sodium hypochlorite (NaCl) (448 g, 0.301 mol, 5% solution) was added in one portion. The solution was stirred for three hours after addition of the sodium hypochlorite, at which point sampling indicated the reaction was complete. The layers were separated, and the aqueous layer was extracted twice with dichloromethane (150 mL). The organic layers were combined, washed with water, dried with magnesium sulfate, filtered, and concentrated on the rotovap to give 60.2 g of 3-chloro-6-trifluoromethyl pyridine.

104.97 g resulting from combining both batches of the crude 3-chloro-6-trifluormethyl pyridine was distilled in an apparatus consisting of a magnetically stirred, 14/20, 250 mL kettle with a 1-piece Vigreaux head with integral condenser, a four fraction distillation receiver, and a heating mantle. Air was used in the condenser to prevent the product from freezing in the condenser, but parts of the distillation apparatus were warmed with a heat gun to melt the product as it distilled. The pressure was established at 160 mmHg and maintained throughout the distillation. Four fractions were collected. The first fraction, 1.86 g, was collected at 103° C. to 106° C. head temperature and consisted of 99.8 area % 3-chloro-6-trifluoromethyl pyridine. The second fraction, 72.76 g, was collected at 107° C. to 108° C. head temperature and consisted of 99.6 area % 3-chloro-6-trifluoromethyl pyridine. The third fraction, 1.8 g, consisted of 97.5% 3-chloro- 6-trifluoromethyl pyridine. The fourth fraction, 1.8 g, consisted of 72.5% 3-chloro-6-trifluoromethyl pyridine with heavier components present. The kettle contained 10.3 g. The second fraction had a melting point of 36° C. to 37° C.

The combined yield for the reaction and distillation (corrected for starting material purity, product GC purity, and incomplete transfer into the distillation apparatus) was 83%.

Example 4

Preparation of 3-chloro-6-trifluoromethyl pyridine

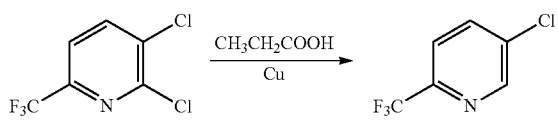

To a 250 mL three-neck round bottom flask, equipped with a reflux condenser and thermowell with digital temperature monitoring, was charged 2,3-dichloro-6-trifluoromethyl pyridine (15 g, 69.4 mmol), copper powder (8.9 g, 138.9 mmol) (two equivalents), and then propionic acid (150 mL). The reaction mixture was heated to 135° C. and allowed to stir for 22 hours. GC analysis indicated that the reaction still contained starting material, so the internal reaction temperature was increased to 145° C., and the reaction mixture was allowed to stir an additional 4.5 hours. GC analysis of the reaction mixture indicated 3-chloro-6-trifluoromethyl pyridine was present in about 92% (by GC relative area) and 2,3-dichloro-6-trifluoromethyl pyridine was present in about 8% (by GC relative area). Heating and stirring was stopped, and the reaction mixture was partitioned between 50 mL of water and 50 mL of hexanes. The reaction mixture was suction filtered through a glass sintered funnel, and the filtrate was washed with 50 mL of hexanes. The combined hexanes layers were washed with three 50 mL portions of saturated aqueous sodium bicarbonate, dried over anhydrous magnesium sulfate, and concentrated on a rotovap at ambient temperature at approximately 20 mmHg to give 7.84 g of 3-chloro-6-trifluoromethyl pyridine (52% yield and a purity of 84% by GC assay) as a white waxy solid. The main impurity was unreacted starting material 2,3-dichloro-6-trifluoromethyl pyridine. IR (diamond/ZnSe) 3060, 1354, 1335, 1130, 1115, 855 cm$^{-1}$. $^1$H NMR (300 MHz, CDCl$_3$) δ 7.66 (d, J=8 Hz, 1H), 7.87 (dd, J=8, 2 Hz, 1H), 8.69 (d, J=1 Hz, 1H). $^{13}$C NMR (75.5 MHz, CDCl$_3$) δ 121.2 (q, J$_{CF}$=275 Hz, CF$_3$), 121.4 (q, J$_{CF}$=3 Hz, CH), 135.2, 137.1, 146.2 (q, J$_{CF}$=36 Hz, C—CF$_3$), 149.1. HRMS (ESI) calcd for C$_6$H$_3$ClF$_3$N m/z 180.9906. Found: 180.9906.

Example 5

Preparation of 6-trifluormethyl-3-ethyl pyridine

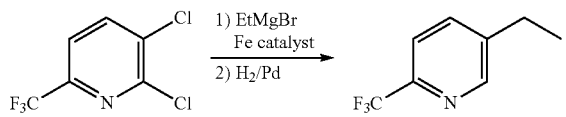

To a 50 mL three-neck round bottom flask was charged iron (III) acetylacetonate (82 mg, 0.23 mmol), 2,3-dichloro-6-trifluoromethyl pyridine (1.00 g, 4.63 mol) in anhydrous tetrahydrofuran (4 mL), and N-methyl-2-pyrrolidinone (NMP) (917 mg, 9.26 mmol) via syringe. The reaction mixture was cooled in an ice-water bath, and then ethyl magnesium bromide (2.0 mL, 16.02 mmol, 3.0 M solution) in diethyl ether solution was added via syringe over a 10 minute period. During the addition of the Grignard reagent, the addition rate was controlled to allow the reaction mixture to rise in temperature from 3° C. to 28° C. The ice-water bath was removed and the reaction mixture was stirred for 10 minutes at which time GC analysis indicated that the reaction was not complete. The reaction mixture was cooled with an ice-water bath. Then, an additional 1.1 mL (3.24 mmol) of 3.0 Methyl magnesium bromide in diethyl ether solution was added via syringe over a 2.5 minute period. The ice water bath was removed and the mixture was allowed to stir for about 5.0 minutes, at which time GC analysis indicated that the starting compound was gone. The mixture was then cooled in a cold water bath and the reaction mixture was quenched with an aqueous ammonium chloride solution (1.0 mL, 30 wt %) and hydrochloric acid (2.0 mL, 1 N solution). Then, ethyl acetate (5 mL) was added to the mixture. The aqueous layer was extracted with ethyl acetate (5 mL). The combined organic layers were partially concentrated on a rotovap at ambient temperature.

The crude oil was dissolved into 10 mL of absolute ethanol and then palladium on carbon (4.0 g, 0.93 mmol, 5%) (this catalyst was about 50.7% wet with water). The mixture was stirred under a hydrogen atmosphere at 30 prig for about 4.5 hours. The reaction mixture was filtered through a pad of celite to give 11.47 g of a dark brown solution. GC analysis of this solution indicated a 6% in-pot yield of the desired 3-ethyl-6-trifluoromethyl pyridine. No further isolation was attempted. GC/EIMS (relative intensity) m/z 175 (87), 160 (100), 140 (15), 106 (41).

Example 6

Preparation of 3-ethyl-6-trifluoromethyl pyridine

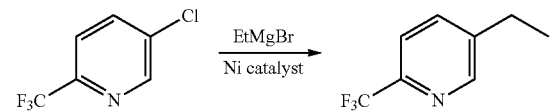

To a dry 250 mL round bottom flask equipped with magnetic stirrer, nitrogen inlet, thermometer, and septum, was charged 3-chloro-6-trifluoromethyl pyridine (1.0 g, 5.5 mmol, 98% purity), Bis-triphenylphosphine nickel (II) dichloride (175 mg, 0.27 mmol), and anhydrous tetrahydrofuran (50 mL). To this mixture was added ethyl magnesium bromide (2.2 mL, 6.6 mmol, 3.0 M solution) in diethyl ether dropwise by syringe. A slight exotherm was noticed and the reaction mixture changed color to a dark purple to black solution. The reaction mixture was stirred at room temperature overnight. The reaction mixture was checked by GC and appeared to include an approximately 1:1 mixture of the starting material and a new peak (longer retention time than the starting material), which showed a mass (GC-MS) consistent with 3-ethyl-6-trifluoromethyl pyridine. Another 100 mg (0.15 mmol) of Bis-triphenylphosphine nickel (II) dichloride and 2.2 mL (6.6 mmol) of ethyl magnesium bromide solution was added to the reaction mixture. Once GC analysis indicated a complete reaction, the mixture was poured into a saturated aqueous ammonium chloride solution (100 mL) and extracted with diethyl ether (3×50 mL). The combined ether extracts were washed with water, brine, dried over anhydrous magnesium sulfate ($MgSO_4$), filtered, and concentrated on a rotovap to produce 0.9 g of crude product. The crude residue was purified by column chromatography on silica gel with a gradient (20 min) of 100% hexane to 50% ethyl acetate, 50% hexane (by volume). The pure fractions were combined and concentrated on a rotovap to produce 0.41 g (42% isolated yield) of 3-ethyl-6-trifluormethyl pyridine as a yellow liquid, which was further confirmed by $^1$H NMR analysis.

Example 7

Preparation of 3-ethyl-6-trifluoromethyl pyridine

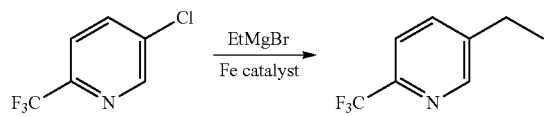

To a dry 250 mL round bottom flask, equipped with magnetic stirrer, nitrogen inlet, thermometer, and septum, was charged 3-chloro-6-trifluoromethyl pyridine (2.0 g, 11.0 mmol), iron (III) phthalocyanine (50 mg, 0.09 mmol), and anhydrous tetrahydrofuran (50 mL). To this mixture was added ethyl magnesium bromide (4.0 mL, 12.1 mmol, 3.0 M solution) in diethyl ether dropwise by syringe. A slight exotherm was noticed and the reaction mixture changed color to a dark solution. The reaction mixture was stirred at room temperature for 2 hours. The reaction mixture was checked by GC and appeared to be an approximately 1:1 mixture of starting material to the desired 3-ethyl-6-trifluormethyl pyridine. The reaction mixture was stirred at ambient temperature overnight. Gas chromatography analysis indicated no change in the reaction mixture. The reaction halted with no further workup.

Example 8

Preparation of 3-ethyl-6-trifluoromethyl pyridine

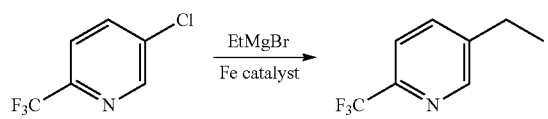

To a 50 mL three-neck round bottom flask was charged iron (III) acetylacetonate (78 mg, 0.22 mmol), 3-chloro-6-trifluoromethyl pyridine (2.00 g, 11.02 mol) in anhydrous tetrahydrofuran (10 mL), and N-methyl-2-pyrrolidinone (NMP) (2.18 g, 22.03 mmol) via syringe. The reaction mixture was cooled in an ice-water bath. Then, ethyl magnesium bromide (4.4 mL, 13.22 mmol, 3.0 M solution) in diethyl ether was added via syringe over a 10 minute period. During the addition of the Grignard reagent, the addition rate was controlled to allow the reaction mixture temperature to rise from 4° C. to 28° C. The ice-water bath was removed, and the reaction mixture was stirred for 10 minutes at which time gas chromatography analysis indicated the reaction was complete. The mixture was then cooled in a cold water bath and the reaction mixture was quenched with aqueous ammonium chloride solution (2.5 mL of 30 wt %). The mixture was allowed to stir for 10 minutes and the organic layer was collected. The bottom aqueous layer was extracted with ethyl acetate (4 mL). The organic layers were combined to give 23.74 g of a dark brown solution. GC analysis of this solution indicated an 81% in-pot yield of the desired 3-ethyl-6-trifluoromethyl pyridine. No further isolation was attempted on this mixture.

Example 9

Preparation of 6-trifluormethyl-5-ethyl pyridine

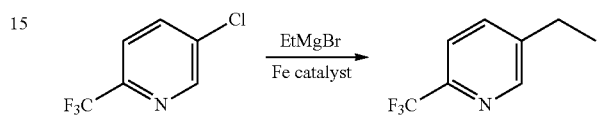

To a 250 mL three-neck round bottom flask was charged iron (III) chloride (268 mg, 1.65 mmol), 3-chloro-6-trifluormethyl pyridine (12.5 g, 68.85 mol, 98% purity) in anhydrous tetrahydrofuran (30 mL), and N-methyl-2-pyrrolidinone (NMP) (13.65 g, 137.7 mmol) via syringe. The reaction mixture was cooled in an ice-water bath, and then ethyl magnesium bromide (29.8 mL, 89.51 mmol, 3.0 M solution) in diethyl ether was added via syringe over a 36 minute period. During the addition of the Grignard reagent, the addition rate was controlled to allow the reaction mixture temperature to rise from 2° C. to 26° C. The ice-water bath was removed and the reaction mixture was stirred for 50 minutes, at which time gas chromatography analysis indicated the reaction was not complete. Another 1.1 mL (3.3 mmol) of 3.0 Methyl magnesium bromide in diethyl ether solution was added via syringe at room temperature. The reaction mixture was stirred for 8.0 minutes and GC analysis indicated that the reaction was not complete. Another 1.0 mL (3.0 mmol) of 3.0 M ethyl magnesium bromide in diethyl ether solution was added via syringe at room temperature. GC analysis of the reaction mixture indicated that the starting material was present in about 2.8% by relative GC area. The mixture was then cooled in a cold water bath and the reaction mixture was quenched with a pre-made solution of ammonium chloride (3.75 g) dissolved in water (8.75 mL) diluted with hydrochloric acid (32 mL, 1N solution) dropwise via addition funnel. To the resulting thick slurry was added ethyl acetate (30 mL). The mixture was allowed to stir for 25 minutes to triturate the slurry. Then, the organic layer was collected. The bottom aqueous layer was extracted with two 24 mL portions of ethyl acetate. The organic layers were combined to give 109.8 g of a dark brown solution. GC assay analysis of this solution indicated a 77% in-pot yield of the desired 3-ethyl-6-trifluoromethyl pyridine. This solution was set aside for further purification.

Example 10

Preparation of 3-ethyl-6-trifluoromethyl pyridine

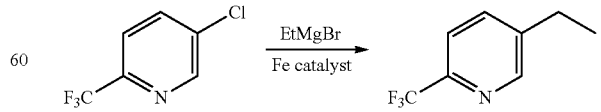

To a 250 mL three-neck round bottom flask was charged iron (III) chloride (268 mg, 1.65 mmol), 3-chloro-6-trifluormethyl pyridine (12.5 g, 68.85 mol, 98% purity) in anhydrous tetrahydrofuran (50 mL), and N-methyl-2-pyrrolidinone (NMP) (13.65 g, 137.7 mmol) via syringe. The reaction mixture was cooled in an ice-water bath. Then, ethyl magnesium bromide (29.8 mL, 89.51 mmol, 3.0 M solution) in diethyl ether was added via syringe over a 23 minute period. During the addition of the Grignard reagent, the addition rate was controlled to allow the reaction mixture temperature to rise from 2° C. to 24° C. The ice-water bath was removed and the reaction mixture was stirred for 13 minutes, at which time GC analysis indicated the reaction was complete. The mixture was then cooled in an ice-water bath and the reaction mixture was quenched with a pre-made solution of ammonium chloride (3.75 g) dissolved in water (8.75 mL) diluted with hydrochloric acid (32 mL, 1 N solution) dropwise via addition funnel. To the resulting slurry was added ethyl acetate (30 mL). The mixture was allowed to stir for 58 minutes to triturate the slurry. Then, the top organic layer was collected. The bottom aqueous layer was extracted with a 25 mL portion of ethyl acetate. The organic layers were combined to give 114 g of a dark brown solution. GC assay analysis of this solution indicated an 84% in-pot yield of the desired 3-ethyl-6-trifluormethyl pyridine.

This solution and the solution resulting from Example 9 were combined. The two combined batches were placed into a 500 mL three-neck round bottom flask. Then 2,6-di-tert-butyl-4-methylphenol (BHT) (50 mg) was added to the mixture. A one-piece micro distillation head with integral condenser was placed onto the flask. A vacuum of about 160 mmHg was applied and the low boiling solvents were removed (b.p. 21° C. to 32° C.). The remaining residue was transferred to a 50 mL three-neck round bottom flask and the same distillation head was attached. The vacuum was then adjusted to 20 mmHg and distillate was collected (b.p. 69° C. to 84° C.) to give 22.91 g. This residue was washed with three 5 mL portions of water to remove the NMP to give 18.62 g (72% isolated yield with a plurality of 94% by GC assay) of 3-ethyl-6-trifluormethyl pyridine as a colorless liquid. This yield was based on the theoretical yield of the combined batches. IR (diamond/ZnSe) 2975, 2940, 2882, 1339, 1175, 1135, 1088, 849 cm$^{-1}$. $^1$H NMR (300 MHz, CDCl$_3$) δ 1.30 (t, J=7 Hz, 3H), 2.75 (q, J=7 Hz, 2H), 7.60 (d, J=8 Hz, 1H), 7.69 (d, J=8 Hz, 1H), 8.57 (s, 1H). $^{13}$C NMR (75.5 MHz, CDCl$_3$) δ 14.9, 25.9, 120.1 (q, J$_{CF}$=3 Hz, CH), 121.8 (q, J$_{CF}$=274 Hz, CF$_3$), 136.4, 142.7, 145.7 (q, J$_{CF}$=35 Hz, C—CF$_3$), 149.8. HRMS (ESI) calcd for C$_8$H$_8$F$_3$N m/z 175.0607. Found 175.0609.

While the invention may be susceptible to various modifications and alternative forms, specific embodiments have been described by way of example in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of forming a 3-substituted-6-trifluoromethyl pyridine, the method comprising reacting a 6-trichloromethyl halogenated pyridine with a fluorinating agent to form a 6-trifluoromethyl halogenated pyridine.

2. The method of claim 1, wherein reacting a 6-trichloromethyl halogenated pyridine with a fluorinating agent to form a 6-trifluoromethyl halogenated pyridine comprises reacting a 6-trichloromethyl-2,3-dihalo pyridine with a fluorinating agent to form a 6-trifluoromethyl-2,3-dihalo pyridine.

3. The method of claim 1, wherein reacting a 6-trichloromethyl halogenated pyridine with a fluorinating agent to form a 6-trifluoromethyl halogenated pyridine comprises reacting a 2,3-dichloro-6-trichloromethyl pyridine with a fluorinating agent to form a 2,3-dichloro-6-trifluoromethyl pyridine.

4. The method of claim 1, wherein reacting a 6-trichloromethyl halogenated pyridine with a fluorinating agent to form a 6-trifluoromethyl halogenated pyridine comprises reacting a 6-trichloromethyl halogenated pyridine with antimony pentafluoride to form a 6-trifluoromethyl halogenated pyridine.

5. The method of claim 1, wherein reacting a 6-trichloromethyl halogenated pyridine with a fluorinating agent to form a 6-trifluoromethyl halogenated pyridine comprises reacting a 6-trichloromethyl halogenated pyridine with hydrogen fluoride to form a 6-trifluoromethyl halogenated pyridine.

6. The method of claim 1, wherein reacting a 6-trichloromethyl halogenated pyridine with a fluorinating agent to form a 6-trifluoromethyl halogenated pyridine comprises reacting a 6-trichloromethyl-(4-halo)-2,3-dichloro pyridine with a fluorinating agent to form a 6-trifluoromethyl-(4-halo)-2,3-dichloro pyridine.

7. The method of claim 1, wherein reacting a 6-trichloromethyl halogenated pyridine with a fluorinating agent to form a 6-trifluoromethyl halogenated pyridine comprises reacting a 6-trichloromethyl-2,3-dichloro pyridine with antimony pentafluoride to form a 2,3-dichloro-6-trifluoromethyl pyridine.

8. The method of claim 1, wherein reacting a 6-trichloromethyl halogenated pyridine with a fluorinating agent to form a 6-trifluoromethyl halogenated pyridine comprises reacting a 6-trichloromethyl-2,3-dichloro pyridine with hydrogen fluoride to form a 2,3-dichloro-6-trifluoromethyl pyridine.

9. The method of claim 1, further comprising reacting the 6-trifluoromethyl halogenated pyridine with a reducing agent to form a 3-halo-6-trifluoromethyl pyridine.

10. The method of claim 9, wherein reacting the 6-trifluoromethyl halogenated pyridine with a reducing agent to form a 3-halo-6-trifluoromethyl pyridine comprises reacting the 6-trifluoromethyl halogenated pyridine with a reducing agent comprising hydrazine and bleach to form a 3-halo-6-trifluoromethyl pyridine.

11. The method of claim 9, wherein reacting the 6-trifluoromethyl halogenated pyridine with a reducing agent to form a 3-halo-6-trifluoromethyl pyridine comprises reacting the 6-trifluoromethyl halogenated pyridine with a reducing agent comprising copper and propionic acid to form a 3-halo-6-trifluoromethyl pyridine.

12. The method of claim 9, wherein reacting the 6-trifluoromethyl halogenated pyridine with a reducing agent to form a 3-halo-6-trifluoromethyl pyridine comprises reacting a 2,3-dichloro-6-trifluoromethyl pyridine with a reducing agent to form a 3-chloro-6-trifluoromethyl pyridine.

13. The method of claim 9, further comprising reacting the 3-halo-6-trifluoromethyl pyridine with a Grignard reagent to form a 3-substituted-6-trifluoromethyl pyridine.

14. The method of claim 13, wherein reacting the 3-halo-6-trifluoromethyl pyridine with a Grignard reagent to form a 3-substituted-6-trifluoromethyl pyridine comprises reacting the 3-halo-6-trifluoromethyl pyridine with a Grignard reagent comprising an alkyl magnesium bromide to form a 6-trifluoromethyl-3-alkyl pyridine.

15. The method of claim 14, wherein reacting the 3-halo-6-trifluoromethyl pyridine with a Grignard reagent comprising an alkyl magnesium bromide to form a 6-trifluoromethyl-3-alkyl pyridine comprises reacting the 3-halo-6-trifluoromethyl pyridine with a Grignard reagent comprising an ethyl magnesium bromide to form a 3-ethyl-6-trifluoromethyl pyridine.

16. The method of claim 13, wherein reacting the 3-halo-6-trifluoromethyl pyridine with a Grignard reagent to form a 3-substituted-6-trifluoromethyl pyridine comprises reacting the 3-halo-6-trifluoromethyl pyridine with a Grignard reagent in the presence of a metal-based catalyst to form a 3-substituted-6-trifluoromethyl pyridine.

17. The method of claim 16, wherein reacting the 3-halo-6-trifluoromethyl pyridine with a Grignard reagent in the presence of a metal-based catalyst to form a 3-substituted-6-trifluoromethyl pyridine comprises reacting the 3-halo-6-trifluoromethyl pyridine with a Grignard reagent in the presence of a nickel-based catalyst to form a 3-substituted-6-trifluoromethyl pyridine.

18. The method of claim 16, wherein reacting the 3-halo-6-trifluoromethyl pyridine with a Grignard reagent in the presence of a metal-based catalyst to form a 3-substituted-6-trifluoromethyl pyridine comprises reacting the 3-halo-6-trifluoromethyl pyridine with a Grignard reagent in the presence of an iron-based catalyst to form a 3-substituted-6-trifluoromethyl pyridine.

19. A method of forming a 3-substituted-6-trifluoromethyl pyridine, the method comprising:
fluorinating a 6-trichloromethyl halogenated pyridine to form a 6-trifluoromethyl halogenated pyridine;
reducing the 6-trifluormethyl halogenated pyridine to form a 3-halo-6-trifluoromethyl pyridine; and
reacting the 3-halo-6-trifluoromethyl pyridine with a Grignard reagent to form the 3-substituted-6-trifluoromethyl pyridine.

20. A method of using a 6-trichloromethyl halogenated pyridine to form a 3-substituted-6-trifluoromethyl pyridine, the method comprising reacting the 6-trichloromethyl halogenated pyridine with at least one of antimony pentafluoride and hydrogen fluoride to form a 6-trifluoromethyl halogenated pyridine.

21. The method of claim 20, further comprising reacting the 6-trifluoromethyl halogenated pyridine with either both hydrazine and sodium hypochlorite or both copper and propionic acid to form a 3-halo-6-trifluoromethyl pyridine.

22. The method of claim 21, further comprising reacting the 3-halo-6-trifluoromethyl pyridine with a Grignard reagent in the presence of at least one of a nickel-based and an iron-based catalyst to form the 3-substituted-6-trifluoromethyl pyridine.

23. The method of claim 20, wherein reacting the 3-halo-6-trifluoromethyl pyridine with a Grignard reagent in the presence of at least one of a nickel-based and an iron-based catalyst to form the 3-substituted-6-trifluoromethyl pyridine comprises reacting the 3-halo-6-trifluoromethyl pyridine with a Grignard reagent in the presence of at least one of a nickel-based and an iron-based catalyst to form a 3-substituted-6-trifluoromethyl pyridine of formula I:

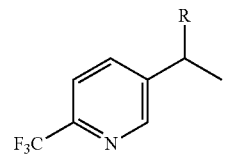

wherein
R represents hydrogen, an alkyl group, or an aryl group.

* * * * *